United States Patent
Nirvanashetty et al.

(10) Patent No.: US 12,208,129 B2
(45) Date of Patent: Jan. 28, 2025

(54) PROCESS FOR PREPARING AN HERBAL EXTRACT AND COMPOSITIONS THEREOF

(71) Applicant: OLENE LIFE SCIENCES PRIVATE LIMITED, Tamil Nadu (IN)

(72) Inventors: Somashekara Nirvanashetty, Chennai (IN); Nilima Mohanty, Chennai (IN); Sanjib Kumar Panda, Chennai (IN); Vivek Anand Parachur, Chennai (IN)

(73) Assignee: OLENE LIFE SCIENCES PRIVATE LIMITED, Chennai (IN)

( * ) Notice: Subject to any disclaimer, the term of this patent is extended or adjusted under 35 U.S.C. 154(b) by 818 days.

(21) Appl. No.: 17/290,506

(22) PCT Filed: Nov. 2, 2019

(86) PCT No.: PCT/IN2019/050811
§ 371 (c)(1),
(2) Date: Apr. 30, 2021

(87) PCT Pub. No.: WO2020/089944
PCT Pub. Date: May 7, 2020

(65) Prior Publication Data
US 2021/0283208 A1    Sep. 16, 2021

(30) Foreign Application Priority Data

Nov. 3, 2018  (IN) .............................. 201841041702

(51) Int. Cl.
*A61K 36/9066*  (2006.01)
*A61K 31/12*  (2006.01)

(52) U.S. Cl.
CPC .......... *A61K 36/9066* (2013.01); *A61K 31/12* (2013.01); *A61K 2236/15* (2013.01); *A61K 2236/333* (2013.01); *A61K 2236/35* (2013.01); *A61K 2236/37* (2013.01); *A61K 2236/51* (2013.01); *A61K 2236/55* (2013.01)

(58) Field of Classification Search
None
See application file for complete search history.

(56) References Cited

U.S. PATENT DOCUMENTS

| | | | |
|---|---|---|---|
| 6,942,881 B2 | 9/2005 | Madsen et al. | |
| 2007/0148263 A1* | 6/2007 | Antony | ..................... A61P 1/18 424/756 |
| 2014/0193533 A1* | 7/2014 | Antony | .................. A61K 31/12 424/756 |

FOREIGN PATENT DOCUMENTS

WO    2015/025263 A1    2/2015

OTHER PUBLICATIONS

International Search Report from International Application No. PCT/IN2019/050811, Olene Life Sciences Private Ltd, dated Jan. 23, 2020.
Naveen Kunta; "Techno-Economic Analysis of Extraction of Curcumin from Turmeric"; A thesis submitted to Oregon State University; Jun. 13, 2018 (Jun. 13, 2018).
Foozie Sahne et al.; "Extraction of Bioactive Compound Curcumin from Turmeric (*Curcuma longa* I. ) via Different Routes: A Comparative Study"; Pakistan Journal of Biotechnology; vol. 13 (3) , pp. 173-180; 2016.
Viviane P. Paulucci et al.; "Optimization of the extraction of curcumin from Curcuma longa rhizomes"; Brazilian Journal of Pharmacognosy; vol. 23 (1) , pp. 94-100; 2013; 9 pgs.

* cited by examiner

*Primary Examiner* — Susan Hoffman
(74) *Attorney, Agent, or Firm* — Kramer & Amado, P.C.

(57) ABSTRACT

The present invention provides a process for preparing an herbal extract such that selective isolation of phytochemicals and resins in specific concentrations is obtained in the final herbal extract and compositions comprising the same. Further, the present invention provides a process for preparing an herbal extract comprising curcuminoids and resins, such that the extract is having high solubility/dispersibility, good bioavailability and efficient sustained release.

11 Claims, 4 Drawing Sheets

PROCESS FOR PREPARING AN HERBAL EXTRACT AND COMPOSITIONS THEREOF

TECHNICAL FIELD OF THE INVENTION

The present invention relates to a process for preparing an herbal extract such that selective isolation of phytochemicals and resins in specific concentrations is obtained in the final herbal extract.

Further, the present invention relates to compositions comprising the said herbal extract consisting of phytochemicals and resins in concentrations ranging from 1% to 90% and 1% to 90%, respectively, wherein the said composition is having high solubility, high bioavailability and sustained release.

BACKGROUND AND PRIOR ART OF THE INVENTION

Plants are recognized in the pharmaceutical industry due to their broad spectrum of structural diversity and their wide range of pharmacological activities. Plants are natural reservoirs of chemical compounds and of structurally diverse bioactive molecules referred to as phytochemicals. A plethora of research studies undertaken have shown plants to be a rich source of compounds called phytochemicals with a wide array of biological activities. Phytochemicals have been employed in scientific studies, influencing the healthcare system in numerous ways such as treating cancer and several other diseases.

The processing of raw plant material is mainly required to optimize the concentrations of known constituents and also to retain their activity. Extraction is an important stage in phytochemical processing for the concentration, identification and application of bioactive constituents from plant materials. The selection of a favourable extraction technique is vital for standardization of herbal constituents in the products as it is utilized in the separating of desirable soluble constituents, leaving out those not required with the aid of solvents. Further, the selection of a suitable extraction process and optimization of various parameters are critical for upscaling purposes.

The extraction techniques most commonly used are conventional techniques such as maceration, percolation, infusion, decoction and hot continuous extraction.

Alternative methods like ultrasound assisted solvent extraction (UASE), microwave assisted solvent extraction (MASE) and supercritical fluid extractions (SFE) have gained interest. The application of these green extraction techniques such as UASE, MASE and SFE have been rapidly increasing for phytochemical processing of medicinal plants as these techniques can be quickly implemented compared to traditional methods.

Ultimately the final extract/product should have good and appropriate biological activity in order to use the extract for therapeutic purpose.

Although phytochemicals are known to possess multiple biological activities, their application is limited by their poor intestinal absorption leading to poor bioavailability. Several strategies are employed to improve the bioavailability of phytochemicals with limited success. Many of the extraction techniques employed for extraction of several phytochemicals are based on maximizing the recovery/yield of phytochemical(s). The conventional extraction methods will lead to the extract containing higher amount of active ingredients but without any bioavailability and slow release.

PCT Publication No. WO2015/025263 discloses a composition for increasing the bioavailability of curcumin, comprising a curcumin mixture and the water extract in a ratio of 70:30, wherein the curcumin mixture comprises curcumin dry crystal, volatile oil, fixed oil and an emulsifier. The process employed in WO'263 mainly focusses on formulation/blending of the standard curcumin using curcumin mixture and the water extract in a ratio of 70:30 along with emulsifier to increase the bioavailability. The inventors of WO'263 do not provide any teaching as regards selective isolation of phytochemicals and resins together in the final herbal extract.

Ion-exchange resin-drug complexes have been used to formulate sustained-release products of acidic and basic drugs. However, there have been no attempts in prior art disclosures to provide an herbal extract comprising phytochemicals and natural resins, such that the said natural resin of the composition confers solubility and sustained release to the phytochemicals of the herbal extract.

U.S. Pat. No. 6,942,881 refers to improving the total yield of curcuminoids from curcuminoid-containing material by repeated extraction of curcuminoids. The said disclosure does not provide for the extraction of an herbal extract containing resin and phytochemicals that possesses properties of high solubility and sustained release.

Herbal formulations available in the art employ synthetic polymers and solubilizers to confer sustained release and solubility/bioavailability to the phytochemical component. However, it would be highly favourable to consumers as well as producers, if sustained release and solubility of the phytochemical constituents is achieved without the use to synthetic emulsifiers. This process has advantages of not using any excipients for increasing the bioavailability and sustained release of phytochemicals.

In the light of the above, there is a lasting need in the art to provide a process for facilitating the selective isolation of phytochemicals along with resins to provide a composition having sustained release activity, high solubility and bioavailability.

Herbal compositions available in literature comprise herbal actives and the process for extraction of herbal actives. So far, there are no prior art disclosures which mention the extract containing active ingredients and resins selectively in specific ranges for enhancing the bioavailability of phytochemicals/herbal actives.

OBJECT OF THE INVENTION

It is an object of the present invention to provide a process for the selective isolation and extraction of 'phytochemicals' and 'resins' in high concentrations from herbal sources.

It is another object of the present invention to provide a bioavailable and sustained release herbal composition comprising 'phytochemical(s)' and 'resins' selectively isolated and extracted by the process of the present invention such that the phytochemical ingredients having high solubility and enhanced bioavailability.

SUMMARY OF THE INVENTION

In an aspect the present invention provides a process for preparing an herbal extract comprising phytochemical (s) and resins, the said process comprising;

(a) grinding an herbal source into a fine powder (10 to 120 mesh);
(b) subjecting the powder to $CO_2$/Solvent extraction to obtain a whole herbal extract containing phytochemical(s)/active ingredients, resin, gums, wax, triglycerides, fatty acids, active ingredients and volatile oils;
(c) subjecting the extract of step(b) to solvent distillation followed by vacuum evaporation to remove solvent;
(d) subjecting the extract of step(c) to steam distillation to remove volatile oils; (e) subjecting the extract of step (d) to extraction with a non-polar solvent to remove soft resins, triglycerides, gums, wax and fatty acids;
(f) subjecting the extract of step(e) to solvent distillation and/or vacuum drying to remove the non-polar solvent and obtain dry flakes;
(g) Milling the flakes of step (f) into a fine powder and vacuum drying the powder to obtain a solvent free and low moisture extract comprising phytochemicals and hard resins;
wherein the concentration of phytochemicals and resins in the powdered extract is in a ratio ranging from 1:9 to 9:1.

In one particular aspect, the present invention provides a process for preparing an herbal extract from *Curcuma longa* comprising Curcuminoids as the phytochemicals and resins. The resin present in the final herbal extract provides solubility/dispersibility, high bioavailability and sustained release profile to the phytochemical in the herbal extract.

In another aspect, the present invention provides an herbal composition having high solubility/dispersibility, high bioavailability and sustained release properties, wherein the said composition comprises the herbal extract obtained by the present process in the powdered form comprising phytochemicals and resins in a ratio ranging from 1:9 to 9:1.

In yet another aspect, the present invention provides an herbal composition with enhanced solubility/dispersibility, bioavailability and sustained release without addition of any external bioavailability enhancers.

Abbreviations

F-3: Herbal extract from *Curcuma longa*
C-95: Standard curcuminoids 95%
CP-01: Curcuminoids with volatile oil containing 85% curcuminoids
OLNP-18: Present composition/Test item

DETAILED DESCRIPTION OF THE DRAWINGS

DETAILED DESCRIPTION OF THE INVENTION

Figure 1:
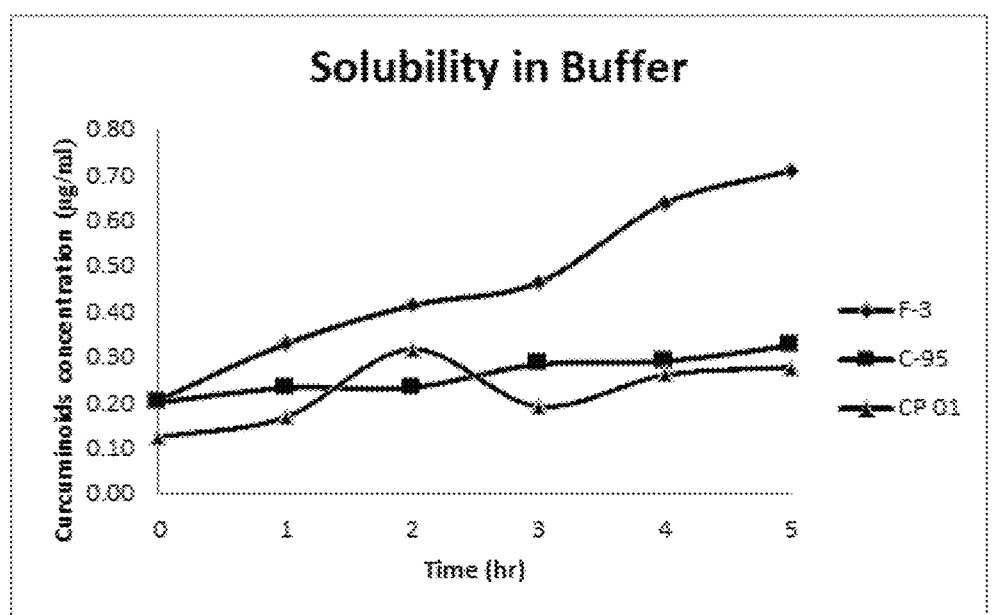
FIG. 1 depicts the solubility of F-3 in comparison with standard curcuminoids 95% (C-95) and Curcuminoids with volatile oil containing 85% Curcuminoids (CP-01) in the buffer.

The invention will now be described in detail in connection with certain preferred and optional embodiments, so that various aspects thereof may be more fully understood and appreciated.

Reference to the term 'phytochemicals' may also be inferred as reference to the term 'herbal actives' or natural active ingredients/compounds.

Source of biological material: Turmeric rhizome is procured from the vendors/farmers in the local markets of the areas such as Erode and Tirunelveli of Tamil Nadu, India.

In a preferred embodiment, the present invention provides a process for preparing an herbal extract comprising phytochemicals and resins, the said process comprising;
(a) grinding a herbal source into a fine powder;
(b) subjecting the powder to $CO_2$/Solvent extraction to obtain a whole herbal extract containing phytochemical(s)/active ingredients, resin, gums, triglycerides (fixed oil), fatty acids, active ingredient, wax and volatile oils;
(c) subjecting the extract of step(b) to solvent distillation and/or vacuum evaporation to remove solvent residues;
(d) subjecting the extract of step(c) to steam distillation to remove volatile oils;
(e) subjecting the extract of step(d) to extraction with a non-polar solvent to remove soft resins, triglycerides (fixed oil), gums, wax and fatty acids;
(f) subjecting the extract of step(e) to solvent distillation or drying/vacuum drying to remove the non-polar solvent and to obtain dry flakes;
(g) milling the flakes of step (f) into a fine powder and vacuum drying the powder to obtain a solvent free and moisture free extract comprising phytochemicals and hard resins;
wherein the concentration of the phytochemicals and resins is in a ratio ranging from 1:9 to 9:1.

The resin present in the final extract provides solubility/dispersibility, bioavailability and sustained release profile to the phytochemical in the extract.

More preferably, the present invention provides a process for the extraction and isolation of phytochemicals and resins in a ratio ranging from 1:5 to 5:1 respectively. Most preferably, the present invention provides a process for the extraction and isolation of phytochemicals and resins in a 1:1 ratio.

In an embodiment, the present invention provides a herb selected from the group comprising *Boswellia serrata, Curcuma longa* (turmeric), *Zingiber officinale* (ginger), *Cinnamomum* sp. (Cinnamon), *Tagetes* sp. (Marigold), *Silybum marianum* (milk thistle), *Xanthorhiza simplicissima* (yellow root), *Allium sativum* (garlic), *Trigonella foenum-graecum* (fenugreek), *Saccharum officinarum* (sugar cane), *Coleus* sp. (*Coleus amboinicus*) and *Commiphora myrrha* (myrrh) Artichoke (*Cynara cardunculus*), *Boswellia, Commiphora mukul* (Myrrh, Guggul), *Curcuma longa, Boswellia serrata, Bacopa monnieri*, Marigold, Ginger, *Glycyrrhiza glabra*, Cinnamon species, *Terminalia chebula, Scutellaria baicalensis, Pinus pinaster* (Maritime pine bark), *Euterpe oleracea* and *Acacia catechu, Silybum marianum, Viscum album, Punica granatum, Camellia sinensis* (Green Tea), Green coffee bean, *Cassia Fistula, Carica papaya, Centella asiatica, Cinnamomum zeylanicum, Cissus quadrangularis, Chlorophytum tuberosum, Curcuma zedoaria, Curcuma xanthorrhiza, Emblica officinalis, Eugenia jambolana, Eurycoma longifolia* Root, *Garcinia cambogia, Garcinia mangostana, Gymnema sylvestre, Indigofera Tinctoria,*

Momordica charantia Fruit (Chamomile), *Moringa citrifolia, Moringa oleifera, Mucuna pruriens, Piper nigrum* Fruit, *Phyllanthus niruri, Salacia oblonga, Salacia reticulata, Sphaeranthus indicus, Sida cordifolia, Tagete serecta* Flower, *Tamarindus indica, Cannabis*, Berberin, *Terminalia arjuna, Terminalia chebula, Tribulus terrestris, Trigonella foenum-graecum*, Triphala, Ashwagandha, resverarol, hupericin, *Guaiacum officinale, G. sanctum* Linn, Garlic, *Allium cepa*, Paprika, colophony resin, *Tetraclinis* articulate (Sandarac resin), *Coleus forskohlii* (frankincense), Shellac, Rosin (s), Dandelion, alfalfa seeds, Milk Thistle, Fenugreek, *Achillea wilhelmsii, Silybum marianum*, Psyllium, Cayenne, Konjac, Basil, Flaxseeds, Hawthorn, Celery, sugar cane, asafetida, *Justicia wynaadensis, Agathos mabetulina, Annona muricata, Apium graveolens, Camellia sinensis, Cassia absus, Cassia occidentalis, Castano spermum austral, Crinum glaucum, Hibiscus sabdariffa, Linumu sitatissimum, Lycopersicone sculentum, Ocimum basilicum, Pinus pinaster, Punica granatum, Rauwolfia serpentine* and *Uncaria rhynchophylla* for extraction of the phytochemical and resin component in the herbal extract. More preferably, the present invention has made use of *Curcuma longa* to obtain an herbal extract comprising curcuminoids and resin in a ratio ranging from 1:9 to 9:1, respectively.

The herbal extract is extracted from plant parts selected from the group comprising rhizome, aerial parts such as leaves, branches, stem, seeds, fruit, flower, exudate or other parts of the aforementioned plants. The selected plant part is ground to a fine powder of mesh size 10 to 120.

In another embodiment, the present invention provides a first solvent for the purpose of extraction is selected from the group comprising $CO_2$, methanol, ethanol, ethyl acetate, acetone, 1-Ethyl-3-(3-dimethylaminopropyl) carbodiimide (EDC), and combinations thereof. The ground powder of step (a) of the present process is subjected to solvent extraction to obtain a whole herbal extract comprising phytochemical (s)/active ingredients, resin, gums, triglycerides (fixed oil), fatty acids, active ingredient, wax and volatile oils; The process of extraction of the said herbal extract in step (b) is performed at a temperature of up to 180° C.

Further, the distillation of solvent comprises a distillation process in step (c) performed at 50° C. to 100° C. and vacuum drying is performed at 1 to 50 mBars vacuum and at a temperature ranging from 10° C. to 80° C.

Further, the distillation of volatile oil comprises steam distillation process in step (d) of the present process to remove/reduce volatile oils In yet another embodiment, the present invention provides nonpolar solvents used in step (e) of the present process for the removal of soft resins, triglycerides, gums, wax and fatty acids from the herbal extract of step (d) is selected from the group comprising non-polar solvents such as n-hexane, hexane, benzene, di-ethyl ether, carbon tetra chloride and methylene chloride etc. In keeping with step (e), the non-polar solvent hexane was added to the herbal extract in a 1:2 ratio, and blended at room temperature. Optionally, heat (up to 50° C.) is applied to facilitate the removal of removal of soft resins, triglycerides, gums, wax and fatty acids from the herbal extract The final drying of the flakes and powder to obtain a final product was done by drying/vacuum drying in a vacuum oven at 1 to 50 mBars vacuum and at a temperature ranging from 10° C. to 80° C., followed by milling into fine powder.

The phytochemicals selectively isolated by the process of the present invention is selected from the group comprising curcuminoids, polyphenolic compounds, alkaloids, flavonoids, terpenes, steroidal compounds etc.

In a particularly preferred embodiment the present invention provides a process for extracting an herbal extract comprising curcuminoids and resins from *Curcuma longa* comprising;
(a) grinding the dry *Curcuma Longa* rhizome parts into a fine powder;
(b) subjecting the powder to $CO_2$ or ethyl acetate or ethanol or methanol extraction to obtain a whole herbal extract containing curcuminoids, resins, gums, triglycerides, fatty acids, wax, gums, active ingredients and volatile oils;
(c) subjecting the extract of step(b) to solvent distillation, concentration/vacuum drying to remove solvent;
(d) subjecting the extract of step(c) to steam distillation to remove volatile oils;
(e) subjecting the extract of step(d) to extraction with a non-polar solvent to remove triglycerides (fat), soft resin fixed oil, wax, gums and fatty acids;
(f) subjecting the extract of step(e) to solvent distillation, drying or vacuum drying to remove the non-polar solvent and obtain dry flakes;
(g) Milling the flakes of step (f) into a fine powder and vacuum drying the powder to obtain a solvent free and low moisture extract comprising curcuminoids and hard resins;
wherein the concentration of the phytochemicals and resins is in a ratio ranging from 1.9 to 9:1.
wherein the total curcuminoids in the final herbal extract contain curcumin in a concentration ranging from 35% to 70% by weight of the total curcuminoids, Demethoxycurcumin in the range of 10 to 40% by weight of the total curcuminoids and Bisdemethoxycurcumin in the range of 10 to 40% by weight of the total curcuminoids.

More specifically, the total curcuminoids in the final herbal extract contain curcumin in a concentration ranging from 55% to 65% by weight of the total curcuminoids, Demethoxycurcumin in the range of 20 to 30% by weight of the total curcuminoids and Bisdemethoxycurcumin in the range of 10 to 20% by weight of the total curcuminoids.

In one preferred embodiment, the present invention provides an herbal extract prepared by the present process comprising curcuminoids and resin in a ratio of 1:9 to 9:1. More preferably, the herbal extract prepared by the present process comprising curcuminoids and resin in a ratio of 1:5 to 5:1. Most preferably, the herbal extract comprises curcuminoids and resin in a ratio of 1:1.

Accordingly, it was observed in the present invention that the process of preparing the herbal extract from *Curcuma longer* yielded curcuminoids and resin in equal proportions. Specific examples demonstrating the same have been exemplified in the present invention.

In one specific embodiment, the present invention provides a powdered form of the herbal extract comprising herbal actives, i.e. curcuminoids in a concentration of 25% to 90% and 45% to 75% resins, respectively. The said herbal extract has a water activity below <0.5 and the residual volatile oil content <5%.

In yet another preferred embodiment the present invention provides an herbal extract comprising curcuminoids >50% by weight of the composition. In a further embodiment, the present invention provides curcuminoids component containing herbal extract consisting of curcumin in a concentration ranging from 35% to 70% by weight of the composition, demethoxycurcumin in a concentration ranging from 10% to 40% by weight of the composition and Bisdemethoxycurcumin in the range of 10 to 40% by weight of the composition.

More specifically, the total curcuminoids in the final herbal extract contain curcumin in a concentration ranging from 55% to 70% by weight of the total curcuminoids, Demethoxycurcumin in the range of 20 to 30% by weight of the total curcuminoids and Bisdemethoxycurcumin in the range of 10 to 20% by weight of the total curcuminoids.

In another preferred embodiment, the present invention provides a bioavailable and sustained release herbal composition comprising an herbal extract consisting of phytochemicals and resins in concentrations ranging from 1% to 90%, and 1% to 90%, respectively.

It has been observed in the present invention that the resin component of the herbal extract obtained by the present process provides solubility/dispersibility, bioavailability and sustained release profile to the phytochemical in the herbal extract and has been demonstrated in the present invention.

FIG. 1 of the present invention shows the solubility profile of the herbal extract obtained by the present process vis-a vis a formulation comprising curcuminoids and volatile oil as well as a simple curcuminoids. The composition comprising the present herbal extract demonstrated enhanced solubility compared to the standard formulations.

Figure 2:
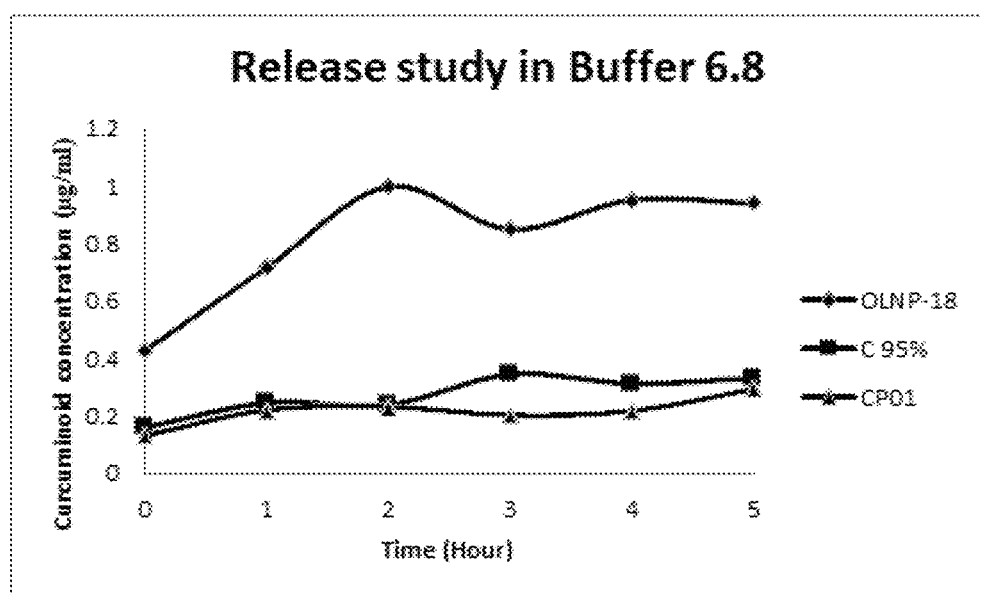
FIG. 2 depicts the solubility profile of the present composition designated as OLNP-18 vis-à-vis the standard curcuminoids 95% (C-95) and Curcuminoids with Volatile oil (CP-01) containing 85% Curcuminoids is given in FIG. 1

Further, FIG. 2 also demonstrates the enhanced solubility profile of the present herbal extract formulated in a composition.

Figure 3:
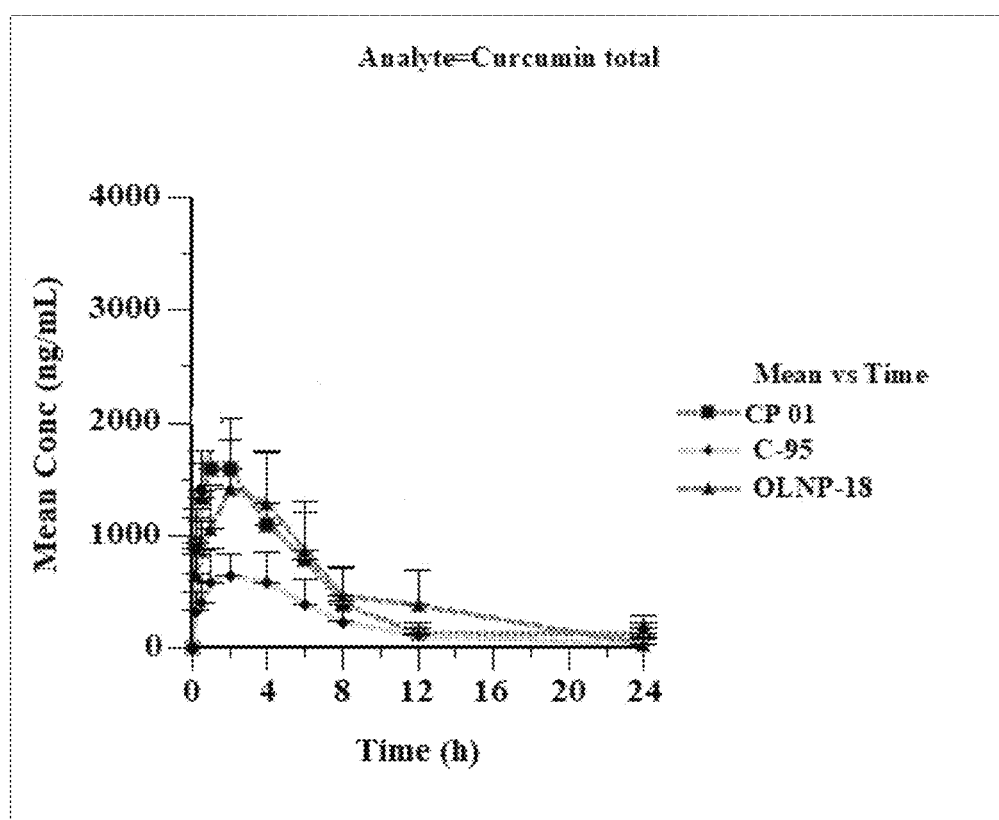
FIG. 3 depicts the bioavailability of Curcumin from the test item (OLNP-18) was increased significantly compared with that of reference formulations, standard curcuminoids 95% (C-95) and CP-01

FIG. 3 depicts the bioavailability of Curcumin from the present herbal extract-test item (OLNP-18) was increased significantly compared with that of reference formulations, Curcuminoids-95% (C-95) and CP 01.

Figure 4:
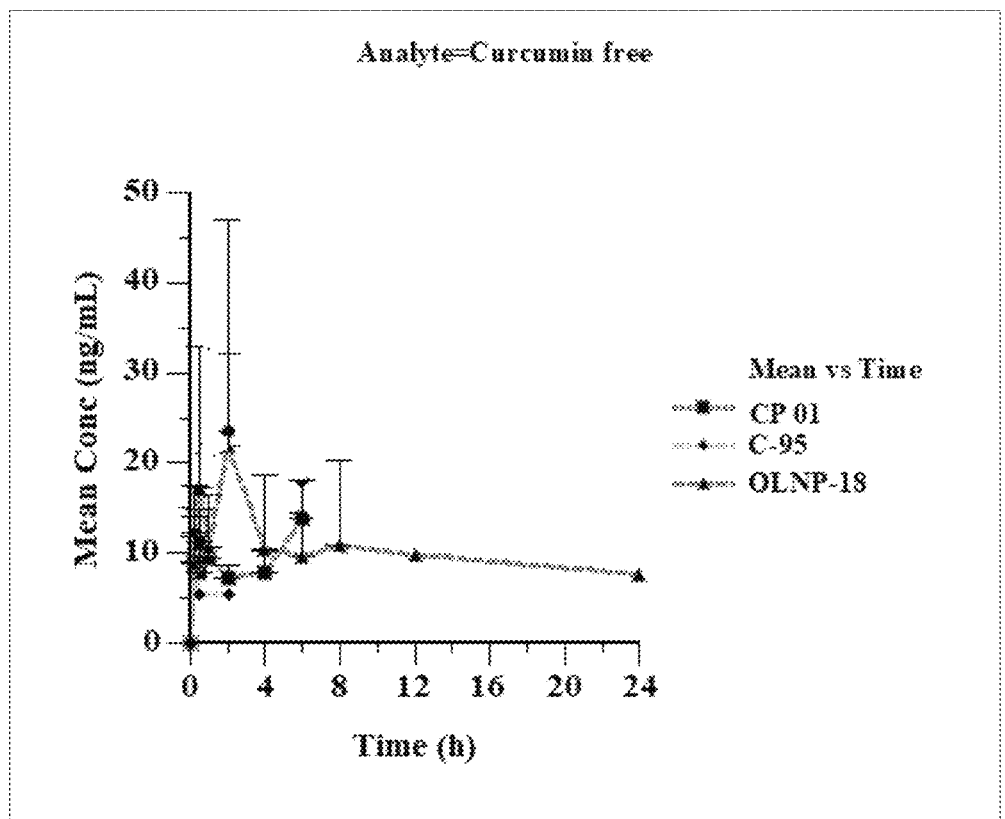
FIG. 4 depicts the sustained release profile of free Curcumin from the test item OLNP-18 over a period of 24 hrs when compared to standard curcuminoids 95% (C-95) and CP-01

More importantly, the herbal extract obtained by the present process exhibits enhanced bioavailability. An exemplified demonstration of the same is observed in Example 6 of the subject patent application. The herbal extract from present invention, OLNP-18 was found to have better oral bioavailability, i.e. a 16% increase compared to a simple formulation comprising Curcuminoids with volatile oils (CP-01); and a 134% increase compared to Standard Curcuminoids comprising 95% Curcuminoids (C-95) (FIG. 4).

Further, the composition may contain pharmaceutically and nutraceutically accepted carriers, excipients, emulsifiers, gliding agents, anti-caking agents, binding agents, polymers (natural or synthetic) to increase the flow properties and adjust the final actives and resin concentration.

In yet another preferred embodiment, the present invention provides the powdered herbal extract obtained by the present process in the form of tablets, capsules, gummies, beverages, lozenges, ready to drink powders and suspensions.

In one more preferred embodiment, the present invention provides the present herbal extract for administration as a nutraceutical composition, pharmaceutical composition and as herbal composition to individuals in need thereof.

EXAMPLES

Following examples are given by way of illustration therefore should not be construed to limit the scope of the invention.

Example 1

Extraction of Herbal Extract from *Curcuma longa*

The dried *C. longa* rhizome was ground into a fine powder. The turmeric powder was extracted with ethyl acetate to obtain a viscous liquid extract containing curcuminoids, gum, wax, fat (fixed oil), fatty acids, volatile oil and resins. The solvent was removed from the extract by distillation. In the next step, volatile oils were removed from the extract by steam distillation. For removal of triglycerides, fixed oil, soft resins, fat, wax, gums, a non-polar solvent such as n-hexane was added to the herbal extract, blended/refluxed for 1 to 6 hrs and the n-hexane layer is separated by filtration, centrifugation/decantation and hexane portion was discarded, thus removing the triglycerides, fixed oil, soft resins, fat, wax, gums from the extract. The extraction with nonpolar solvent is repeated for 4 to 7 times to ensure the complete removal of triglycerides, fixed oil, soft resins, wax, fat and gums. Post removal of the extracting solvent, the herbal extract was vacuum dried (temperature; 60° C., Vacuum: 12 mBars) to obtain hard/solid dry flakes. The flakes obtained are milled into fine powder in a communiting mill to obtained powder with particle size of 40 to 170 mesh. The milled powder was vacuum dried in a vacuum dryer for up to 12 hours at a vacuum of 12 mBars to get a free flowing powder with low moisture. The powdered form of the herbal extract comprises herbal actives, i.e. curcuminoids in a concentration of 25% to 90% and 45% to 75% resins with water activity below <0.5 and volatiles oils <5%.

The examples illustrated herein below specifically demonstrate the process for extraction of the herbal actives and resins in specific concentrations.

Example 2

Extraction of Herbal Extract Designated F2 from *Curcuma longa*

The dried *C. longa* rhizome was ground into a fine powder. The total curcuminoids content in this powder was in the range of 2-3%. The turmeric powder was extracted with ethyl acetate to obtain a liquid extract containing curcuminoids, fat (fixed oil), fatty acids, gums, wax, volatile oil and resins. The curcuminoids content in this extract was >20%. The solvent was removed from the extract by distillation at 75° C. to 80° C. In the next step, volatile oils are removed from the extract by steam distillation. For removal of triglycerides, fixed oil, soft resins, fat, wax, gums from the extract, a non-polar solvent hexane was added to the herbal extract in 1:2 ratio, blended at room temperature and the hexane layer is separated by filtration, centrifugation/decantation and discarded. The process is repeated for 4 to 7 cycles thus removing the triglycerides, fixed oil, soft resins, fat, gums, wax, fatty acids from the extract. Post removal of the extracting solvent, i.e. hexane, the extract was then vacuum dried for up to 12 hours at a vacuum of 12 mBars at 35° C. to 60° C. get hard flakes. The obtained flakes were then milled in a communiting mill to obtain a free flowing powder with particle size of more than 40 mesh. The final product was tested using HPLC and the results are shown in Table 1.

TABLE 1

| Total Curcuminoids by HPLC of example 2 (F-2) | |
|---|---|
| Curcuminoids Content | g/100 g |
| Curcumin | 29.21 |
| Bisdemethoxycurcumin | 8.71 |
| Demethoxycurcumin | 11.45 |
| Total Curcuminoids | 49.37 |

The total curcuminoids content in the final product of Example 2 was 49.37%, wherein the curcumin content was 59.17%, Demethoxycurcumin was 23.19% and Bisdemethoxycurcumin was 17.64% of the total curcuminoids. The total content of the resin in the final product is 50.63%.

Example 3

Extraction of Herbal Extract Designated F3 from *Curcuma longa*

The dried *C. longa* rhizome was ground into a fine powder. The turmeric powder was extracted with ethyl acetate to obtain a liquid extract containing curcuminoids, fat, gums, wax, fatty acids, volatile oil and resins. The solvent is removed from the extract by distillation at 75° C. to 80° C. In the next step, volatile oils were removed from the extract by steam distillation. For removal of triglycerides, fixed oil, soft resins, fat, gums and wax a non-polar solvent, hexane was added to the herbal extract in a 1:2 ratio, blended at room temperature and the hexane layer was separated by filtration and discarded. The process is repeated for 4 to 7 cycles thus removing the triglycerides, fixed oil, soft resins, fat, wax and gums from the extract. Post removal of the extracting solvent, i.e. hexane, the extract was then vacuum dried for up to 12 hours at a vacuum of 12 mBars at 35° C. to get hard/dry flakes. The obtained flakes were then milled in a communiting mill to obtain a free-flowing powder with particle size of 120 mesh. The final product was tested using HPLC and the results are shown in Table 2.

TABLE 2

Total Curcuminoids by HPLC of Example 3 (F-3)

| Curcuminoids Profile | g/100 g |
|---|---|
| Curcumin | 32.49 |
| Demethoxycurcumin | 12.75 |
| Bisdemethoxycurcumin | 9.88 |
| Total Curcuminoids | 55.12 |

The total curcuminoids content in the final product of Example 2 was 55.12%, wherein the curcumin content was 58.9%, Demethoxycurcumin was 23.13% and Bisdemethoxycurcumin was 17.9% of the total curcuminoids. The total content of the resin in the final product is 44.88%.

Example 4

Solubility for the final product (F-3) from Example 3:

Solubility of F-3 was done in phosphate buffer 6.8 in comparison with standard curcuminoids(C-95) and Curcuminoids with volatile oil containing 85% Curcuminoids (CP 01) (Curcuminoids with volatile oil standardised to 86% curcuminoids). 500 mg each of F-3 powder, standard curcuminoids (C-95) and CP 01 was added into 500 ml of 6.8 buffer in separate beakers. All the beakers containing test products and buffer were kept in water bath with temperature of 37° C. with continuous stirring. Samples were collected at regular intervals (0, 1, 2, 3, 4 and 5 hrs), filtered using Whatman filter paper and analysed for Curcumin content by using UV-Spectrophotometer. The solubility profile of the test products are given in FIG. 1

Example 5

Extraction of Herbal Extract Designated OLNP-18 from *Curcuma longa*

The dried *C. longa* rhizome was ground into a fine powder. The turmeric powder was extracted with ethyl acetate to obtain a viscous liquid extract containing curcuminoids, gum, wax, fat (fixed oil), fatty acids, volatile oil and resins. The solvent was removed from the extract by distillation at 75° C. to 85° C. In the next step, volatile oils were removed from the extract by steam distillation. For removal of triglycerides, fixed oil, soft resins, fat, gums, wax, a non-polar solvent, hexane was added to the herbal extract in 1:2 ratio, blended at 30° C. to 45° C. and the hexane layer is separated by decantation and filtration, and hexane portion was discarded. The extraction with non-polar solvent is repeated for 6 times to ensure the complete removal of triglycerides, fixed oil, soft resins, fat, wax and gums. Post removal of the extracting solvent, i.e. hexane, the extract was then vacuum dried for 12 hours at a vacuum of 12 mBars at 60° C. to get hard dry flakes. The obtained flakes were then milled in a communiting mill to obtain a free-flowing powder with particle size of more than 120 mesh. The final product was tested using HPLC and the results are shown in Table 3.

TABLE 3

Total Curcuminoids content of OLNP-18

| Curcuminoids Content | g/100 g |
|---|---|
| Curcumin | 30.36 |
| Demethoxycurcumin | 12.20 |
| Bisdemethoxycurcumin | 8.80 |
| Total Curcuminoids | 51.36 |

The total curcuminoids content in the final product of Example 5 was 51.36%, wherein the curcumin content was 59.11%, Demethoxycurcumin was 23.75% and Bisdemethoxycurcumin was 17.13% of the total curcuminoids. The total content of the resin in the final product is 48.64%.

Example 6

Comparative Bioavailability Studies of the OLNP-18 Composition of the Present Invention Vis-à-Vis CP-01 and Standard Curcuminoids (C-95%)
CP-01=Curcuminoids with Volatile Oil
Standard Curcuminoids (C-95%): Standard Turmeric Extract The Pharmacokinetics of OLNP-18 in comparison with CP-01 and Standard Curcuminoids (C-95%) following single oral administration (500 mg/Kg BW; equivalent to Curcuminoids) was carried out in Male Wistar Rats. Following dose administration, blood was collected from each animal at 0.00, 1.00, 2.00, 3.00, 4.00, 6.00, 8.00, 10.00, 12.00 and 24.00 hours. Plasma was separated in pre-labelled vials after centrifugation at 3000 RPM for 10 mins. at 4° C. and stored at −70° C. until the bioanalysis. A partially validated LC-MS/MS method was used to quantify Curcumin in Rat plasma.

None of the rats exhibited any signs of toxicity during the experimental period. No mortality or morbidity was observed during the experimental period.

The study findings revealed that bioavailability of Curcumin from the test item (OLNP-18) were increased significantly compared with that of reference formulations, Standard Curcuminoids (C-95%) and CP-01 (FIG. 3). OLNP-18 was found to have better oral bioavailability (16% →) than CP-01; and (134% →) than Standard Curcuminoids (C-95%). OLNP-18 showed 116% and 234% relative bioavailability (AUCs) as compared to CP-01 and Standard Curcuminoids (C-95%), respectively for Curcumin. OLNP-18 showed sustained release profile for free Curcumin over a period of 24 hrs compare to CP-01 and Standard Curcuminoids (C-95%) (FIG. 4). It showed approximately 3-fold higher AUCs as compared to CP-01 and approximately 11-fold higher AUCs as compared to Standard Curcuminoids (C-95%) for free curcumin. Exposures (AUCs) ordered in ascending manner: OLNP-18>CP01>C95.

Under this experimental conditions, OLNP-18 was found to superior to Standard Curcuminoids (C-95%) and CP-01 in increasing the bioavailability and sustained release profile of Curcumin in male Wistar Rats.

Example 7

Release Profile of OLNP-18

Release study of OLNP-18 was done in phosphate buffer 6.8 in comparison with standard curcuminoids 95% (C-95) and the Curcuminoids formulation with volatile oils (CP-01). 500 mg each of OLNP-18 powder, standard curcuminoids 95% and CP-01 was added into 400 ml of 6.8 buffer in separate beakers kept in water bath at the temperature of 37° C. with continuous stirring. Samples were collected at regular intervals (0, 1, 2, 3, 4 and 5 hrs), filtered using Whatman filter paper and analysed for Curcumin content by using UV-Spectrophotometer. The solubility profile of the test products is given in FIG. 2.

Advantages of the Present Invention

The herbal extract comprising phytochemicals and resins is obtained by a simple process of the present invention. The present process does not require separate extraction processes which are usually observed in conventional processes.

The resultant herbal extract comprising phytochemicals and resins (i.e. curcuminoids and resin) is having high solubility, high bioavailability and sustained release.

The herbal extract will have the curcuminoids profile similar to that of Turmeric rhizome, a natural curcuminoids profile.

The herbal extract is free from any synthetic emulsifiers or bio-enhancers, hence very safe for oral consumption

We claim:
1. A process for preparing an herbal extract comprising a phytochemical and a resin, comprising;
(a) grinding an herbal source into a fine powder;
(b) subjecting the fine powder to extraction with an extraction solvent to obtain an herbal extract comprising the phytochemical, the resin, a gum, a wax, a triglyceride, a fatty acid, a fixed oil, and a volatile oil; wherein the extraction solvent is $CO_2$, ethyl acetate, acetone, 1-ethyl-3-(3-dimethylaminopropyl) carbodiimide, or a mixture thereof;
(c) removing the extraction solvent from the herbal extract of step (b);
(d) subjecting the herbal extract of step (c) to steam distillation to remove the volatile oil;
(e) subjecting the herbal extract of step (d) to extraction with a non-polar organic solvent to remove the gum, the fixed oil, the wax, the triglyceride, and the fatty acid;
(f) removing the non-polar solvent from the extract of step (e) to obtain dry flakes;
(g) milling the dry flakes of step (f) into a milled powder and vacuum drying the milled powder to obtain a solvent free and low moisture extract comprising the phytochemical and the resin;
wherein the phytochemical and the resin are present in a ratio ranging from 1:9 to 9:1 by weight,
wherein the phytochemical is a curcuminoid.

2. The process for preparing an herbal extract as claimed in claim 1, wherein:
the step of subjecting the fine powder to extraction in step (b) is performed at a temperature of up to 180° C. with the extraction solvent, wherein the extraction solvent is ethyl acetate, acetone, 1-ethyl-3-(3-dimethylaminopropyl) carbodiimide, or a mixture thereof; and
removing the extraction solvent in step (c) comprises subjecting the extract of step (b) to solvent distillation to remove the extraction solvent, followed by drying the extract of step (b) under vacuum.

3. The process for preparing an herbal extract as claimed in claim 2, wherein:
removing the extraction solvent in step (c) comprises subjecting the extract of step (b) to solvent distillation at 50° C. to 100° C. to remove the organic solvent, followed by
drying the extract of step (b) under vacuum at a pressure of 1 to 50 mBars and at a temperature of 10° C. to 80° C.

4. The process for preparing an herbal extract as claimed in claim 1, wherein:
step (e) comprises extraction with a non-polar organic solvent; and
the non-polar organic solvent is selected from the group consisting of n-hexane, hexane, benzene, diethyl ether, carbon tetra chloride, methylene chloride, and combinations thereof.

5. The process for preparing an herbal extract as claimed in claim 1, wherein:
step (e) comprises extraction with a non-polar organic solvent;
the non-polar organic solvent is a hexane solvent; and
the hexane solvent and the herbal extract are mixed in a 1:2 ratio and blended at room temperature.

6. A process for extracting a curcuminoid and a hard resin from *Curcuma longa*, comprising;
(a) grinding a dry *Curcuma longa* rhizome into a fine powder;
(b) subjecting the fine powder to extraction with an extraction solvent to obtain an herbal extract containing the curcuminoid, the resin, a gum, a wax, a triglyceride, a fixed oil, a fatty acid, and a volatile oil;
wherein the extraction solvent is $CO_2$, ethyl acetate, acetone, or a mixture thereof;
(c) removing the extraction solvent from the herbal extract of step (b);
(d) subjecting the herbal extract of step (c) to steam distillation to remove the volatile oil;
(e) subjecting the herbal extract of step (d) to extraction with a non-polar solvent to remove the gum, the wax, the triglyceride, the fixed oil, and the fatty acid;
(f) removing the non-polar solvent from the extract of step (e) to obtain dry flakes;

(g) milling the dry flakes of step (f) into a milled powder and vacuum drying the milled powder to obtain a solvent free and low moisture product comprising the curcuminoid and the resin;
wherein the curcuminoid and the resin are present in the product in a ratio ranging from 1:9 to 9:1 by weight.

7. The process as claimed in claim 6, wherein the solvent free and low moisture product comprises the curcuminoid in a concentration of 25% to 90% and the resin in a concentration of 45% to 75%.

8. The process as claimed in claim 6, wherein the curcuminoid is selected from the group consisting of curcumin, demethoxycurcumin, bisdemethoxycurcumin, and a mixture thereof.

9. The process as claimed in claim 8, wherein the curcuminoid comprises a mixture of:
curcumin in a concentration ranging from 55% to 70% by weight of the curcuminoid,
demethoxycurcumin in a concentration ranging from 20% to 30% by weight of the curcuminoid; and
bisdemethoxycurcumin in the range of 10 to 20% by weight of the curcuminoid.

10. The process as claimed in claim 8, wherein the herbal extract comprises a mixture of:
curcumin in a concentration ranging from 35% to 70% by weight of the extract,
demethoxycurcumin in a concentration ranging from 10% to 40% by weight of the extract; and
bisdemethoxycurcumin in the range of 5% to 40% by weight of the extract.

11. A process for preparing an herbal extract comprising a phytochemical and a hard resin, comprising;
(a) grinding an herbal source into a fine powder;
(b) subjecting the fine powder to extraction with an extraction solvent to obtain an herbal extract comprising the phytochemical, a soft resin, the hard resin, a gum, a wax, a triglyceride, a fatty acid, a fixed oil, and a volatile oil;
wherein the extraction solvent is $CO_2$, ethyl acetate, acetone, or a mixture thereof;
(c) removing the extraction solvent from the herbal extract of step (b);
(d) subjecting the herbal extract of step (c) to steam distillation to remove the volatile oil;
(e) subjecting the herbal extract of step (d) to extraction with hexane to remove the gum, the soft resin, the fixed oil, the wax, the triglyceride, and the fatty acid;
(f) removing the hexane from the extract of step (e) to obtain dry flakes;
(g) milling the dry flakes of step (f) into a milled powder and vacuum drying the milled powder to obtain a solvent free and low moisture extract comprising the phytochemical and the hard resin;
wherein the phytochemical and the hard resin are present in a ratio ranging from 1:9 to 9:1 by weight, wherein the phytochemical is a curcuminoid.

* * * * *